US012738091B2

(12) United States Patent
Zhu et al.

(10) Patent No.: US 12,738,091 B2
(45) Date of Patent: Sep. 15, 2026

(54) ADAPTABLE CAMERA-BASED CONTACTLESS SpO2 DETECTION

(71) Applicant: Samsung Electronics Co., Ltd., Suwon-si (KR)

(72) Inventors: Li Zhu, Saratoga, CA (US); Qijia Shao, New York, NY (US); Mohsin Ahmed, Sunnyvale, CA (US); Korosh Vatanparvar, San Jose, CA (US); Migyeong Gwak, Santa Clara, CA (US); Nafiul Rashid, San Jose, CA (US); Jungmok Bae, Menlo Park, CA (US); Jilong Kuang, San Jose, CA (US); Jun Gao, Menlo Park, CA (US)

(73) Assignee: Samsung Electronics Co., Ltd., Suwon-si (KR)

( * ) Notice: Subject to any disclaimer, the term of this patent is extended or adjusted under 35 U.S.C. 154(b) by 150 days.

(21) Appl. No.: 18/759,674

(22) Filed: Jun. 28, 2024

(65) Prior Publication Data

US 2025/0087016 A1 Mar. 13, 2025

Related U.S. Application Data

(60) Provisional application No. 63/537,085, filed on Sep. 7, 2023.

(51) Int. Cl.
*G06V 40/10* (2022.01)
*A61B 5/1455* (2006.01)
(Continued)

(52) U.S. Cl.
CPC .............. *G06V 40/15* (2022.01); *G06V 10/56* (2022.01); *G06V 10/764* (2022.01);
(Continued)

(58) Field of Classification Search
CPC . A61B 5/14552; A61B 5/0075; A61B 5/0077; A61B 5/14551; A61B 5/7267;
(Continued)

(56) References Cited

U.S. PATENT DOCUMENTS 10,521,900 B2 12/2019 Bartula
11,020,030 B2 6/2021 Tao
(Continued)

FOREIGN PATENT DOCUMENTS

CN 112869737 A 6/2021
CN 113397535 A 9/2021
(Continued)

OTHER PUBLICATIONS

Petersen,et al., "Remote Estimation of Peripheral Oxygen Saturation and Pulse Rate From Facial Analysis Using a Smartphone Camera*," 45th Annual International Conference of the IEEE Engineering in Medicine & Biology Society (EMBC), Sydney, Australia, 2023, pp. 1-4,doi: 10.1109/EMBC40787.2023.10340995 (Year: 2023).*

(Continued)

*Primary Examiner* — Matthew C Bella
*Assistant Examiner* — Janice E. Vaz

(57) ABSTRACT

In one embodiment, a method includes recording, by a camera of a client device, a video of a region of a first user's skin and estimating, from the recorded video, a current ratio of ratios (RoR) for the first user corresponding to the first user's current blood-oxygen saturation. The method further includes converting the first user's determined RoR to a transformed RoR for the first user based at least in part on a baseline user's RoR determined while generating a trained SpO2 prediction model. The trained SpO2 prediction model is trained to estimate the baseline user's SpO2 value based on an input RoR value from the baseline user. The method (Continued)

further includes determining, by the trained SpO2 prediction model and based on the transformed RoR for the first user, the first user's current estimated blood-oxygen saturation.

20 Claims, 11 Drawing Sheets

(51) Int. Cl.

| | |
|---|---|
| ***G06V 10/56*** | (2022.01) |
| ***G06V 10/764*** | (2022.01) |
| ***G06V 10/774*** | (2022.01) |
| ***G06V 20/40*** | (2022.01) |
| ***H04N 23/611*** | (2023.01) |
| ***H04N 23/71*** | (2023.01) |
| ***H04N 23/72*** | (2023.01) |
| ***H04N 23/74*** | (2023.01) |
| ***H04N 23/84*** | (2023.01) |

(52) U.S. Cl.
CPC ............ *G06V 10/774* (2022.01); *G06V 20/41* (2022.01); *H04N 23/611* (2023.01); *H04N 23/71* (2023.01); *H04N 23/72* (2023.01); *H04N 23/74* (2023.01); *A61B 5/14552* (2013.01); *G06V 2201/03* (2022.01); *H04N 23/84* (2023.01)

(58) Field of Classification Search
CPC .. A61B 5/1495; G06V 40/15; G06V 2201/03; G06V 10/56; G06V 10/764; G06V 20/41; G06V 10/774; H04N 23/84; H04N 23/611
See application file for complete search history.

(56) References Cited

U.S. PATENT DOCUMENTS

| | | | |
|---|---|---|---|
| 11,229,372 B2 | 1/2022 | Tao | |
| 11,324,406 B1 | 5/2022 | Nour | |
| 11,432,727 B2 | 9/2022 | Han | |
| 2007/0024946 A1 | 2/2007 | Panasyuk | |
| 2016/0113531 A1 | 4/2016 | Visvanathan | |
| 2017/0238805 A1 | 8/2017 | Addison | |
| 2018/0153455 A1 | 6/2018 | Guazzi | |
| 2021/0015376 A1 | 1/2021 | Kim | |
| 2021/0153752 A1 | 5/2021 | Park | |
| 2022/0409078 A1 | 12/2022 | Sperrhake | |
| 2023/0000377 A1* | 1/2023 | Wu | A61B 5/02416 |
| 2023/0091866 A1 | 3/2023 | White | |
| 2024/0016424 A1 | 1/2024 | Zhu | |

FOREIGN PATENT DOCUMENTS

| | | |
|---|---|---|
| CN | 114758400 A | 7/2022 |
| EP | 3 838 128 A1 | 6/2021 |
| EP | 4076186 A0 | 6/2021 |
| JP | 2018-038553 | 3/2018 |
| JP | 2021-153878 | 10/2021 |
| KR | 10-2015-0095661 | 8/2015 |
| KR | 10-2411622 B1 | 6/2022 |
| WO | WO 2023-091576 A1 | 5/2023 |

OTHER PUBLICATIONS

Extended European Search Report in Application No. 23839982.8-1113 /4518755 PCT/KR2023009997, Mar. 18, 2025.

"Noncontact Monitoring of Blood Oxygen Saturation Using Camera and Dual-Wavelength Imaging System" Shao et al., IEEE Transactions on Biomedical Engineering, vol. 63, No. 6, Jun. 2016.

PCT International Search Report in Application No. PCT/KR2023/009997, Oct. 26, 2023.

PCT Written Opinion of the International Searching Authority in Application No. PCT/KR2023/009997, Oct. 26, 2023.

PCT International Search Report and Written Opinion in Application No. PCT/KR2024/012340, Nov. 22, 2024.

Non-final office action in U.S. Appl. No. 18/213,461, Mar. 10, 2026.

Guazzi et al., "Non-contact measurement of oxygen saturation with an RGB camera." Biomedical Optics Express, Aug. 11, 2015.

Extended European Search Report in Application No. 24863072.5-113/4673048 PCT/KR2024012340, Mar. 11, 2026.

Chan, Michael et al. "Estimating SpO2 with Deep Oxygen Desaturations from Facial Video Under Various Lighting Conditions: A Feasibility Study"; 2023 45th Annual International Conference of the IEEE Engineering in Medicine & Biology Society , IEEE, Jul. 24, 2023, pp. 1-5, Jul. 24, 2023.

Li, Zhu, et al: "Contactless SpO2 Detection from Face Using Consumer Camera"; 2022 IEEE-EMBS International Conference on Wearable and Implantable Body Sensor Networks (BSN), IEEE, pp. 1-4, Sep. 27, 2022.

Notice of Allowance in U.S. Appl. No. 18/213,461, Jul. 7, 2026.

Communication pursuant to Article 94(3) EPC in EPO Application No. 23 839 982.8-1113, Apr. 9, 2026.

* cited by examiner

ADAPTABLE CAMERA-BASED CONTACTLESS SpO2 DETECTION

PRIORITY CLAIM

This application claims the benefit under 35 U.S.C. § 119 of U.S. Provisional Patent Application No. 63/537,085 filed Sep. 7, 2023, which is incorporated by reference herein.

TECHNICAL FIELD

This application generally relates to adaptable camera-based contactless SpO2 detection.

BACKGROUND

Changes in blood volume in the blood vessels of a human body relate to important physiological phenomena. For example, blood-volume pulses correspond to a person's heartbeat and blood pressure. In addition, changes in blood volume can be used to estimate oxygen levels in a person's blood. For example, changes in blood volume can provide information about oxygen saturation (SpO2), which is a measure of the percentage of oxygen-bounded hemoglobin over the total hemoglobin in a user's blood.

DESCRIPTION OF EXAMPLE EMBODIMENTS

The oxygen saturation of a person's blood (SpO2 or SaO2) can be measured using an arterial blood gas test. This test requires taking a blood draw from a person's artery and must be performed in a clinical setting. The test is invasive and painful, and is not continuous in that each blood draw only provides information about a person's SaO2 at the point in time corresponding to the blood draw. In addition, the arterial blood gas test does not provide immediate results because the drawn blood must be sent to a lab for analysis.

A finger pulse oximeter is a non-invasive test that uses light to estimate a person's SpO2. However, a finger pulse oximeter requires continuous contact with a person's finger, e.g., by being clamped to the finger, and therefore the test does not provide a convenient measurements of a person's SpO2-particularly continuous measurements, as those would require a person to leave the pulse oximeter attached to their finger over time, limiting use of that hand. In addition, because a finger pulse oximeter requires contact with a person's finger, this approach can spread infections when the same oximeter is used by different people.

Non-invasive SpO2 measurements that use light rely on a ratio-of-ratios technique to estimate SpO2 in a person's blood. When light from a light source is incident on a person's skin, some of the incident light reflects off the surface of a person's skin, known as specular reflection, and some of the light passes into the person's tissue. The person's tissue also reflects some light, and some of this reflected light may travel back through the person's tissue and pass out of the person's skin, known as diffuse reflection. A light sensor can capture both light from specular reflection and light from diffuse reflection. The characteristics of specular and diffuse reflection depend in-part on the wavelength of incident light. The ratio-of-ratios is derived based on the differential absorption of oxygenated hemoglobin (HbO2) and deoxygenated hemoglobin (HbR) at two or more different wavelengths, which correlates with blood oxygen saturation.

Figure 1:
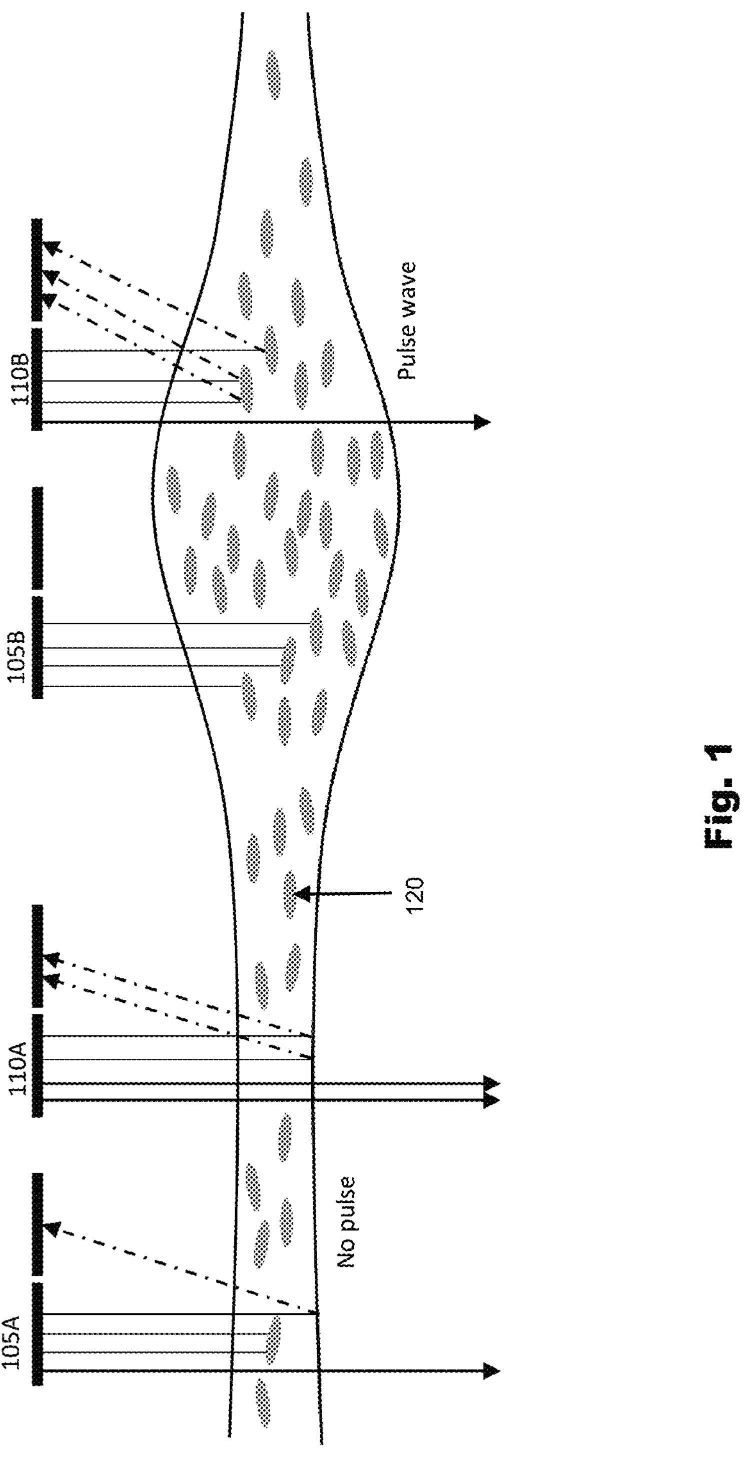
FIG. 1 illustrates an example of light interacting with blood in a person's artery.

Diffuse reflection can vary based on the amount of blood that the light interacts with. FIG. 1 illustrates a simplified example in which light 105A-B having a first wavelength (e.g., green light) and light 110A-B having a second wavelength (e.g., red light) interacts with blood in a person's artery. The blood contains several red blood cells 120. As illustrated in FIG. 1, when the blood is not subject to a pulse, then some light 105A is absorbed by red blood cells, some is reflected off the person's tissue, and some passes through the person's tissue. Some light 110A is reflected off the person's red blood cells and tissue, and some light 110A passes through the person's tissue. However, when the person's blood is subject to a pulse, the number of red blood cells 120 increases in a given arterial region, and as a result, light 105B is more likely to be absorbed by red blood cells 120 while light 110B is more likely to be reflected off of red blood cells 120. Thus, the relative reflectance of different wavelengths of light when the blood is static vs. pulsed indicates the presence of red blood cells, which correspond to blood-oxygen levels.

More formally, the light $R_c$, for a given wavelength c, reflected off a person's skin is represented by:

$$R_c = \sum_{\lambda_c} L(\lambda, \vec{x}, t) s(\lambda, \vec{x}, t) r_c(\lambda, t),$$

where $r_c(\lambda, t)$ represents the sensor response for a given wavelength c; $s(\lambda, \vec{x}, t)$ represents the light reflectance, which is equal to $=m(\lambda, \vec{x})\, b(\lambda, \vec{x}, t)$; and $L(\lambda, \vec{x}, t)$ represents the incident light, which is equal to $=l(\vec{x}, t)\hat{L}(\lambda)$. In these equations, $m(\lambda, \vec{x})$ corresponds to specular reflection, which represents the effect from n non-blood tissue (e.g., melanin, water, etc.). $b(\lambda, \vec{x}, t)$ corresponds to diffuse reflect, which represents the effect from blood-light interactions. $\hat{L}(\lambda)$ represents the spectral distribution of the incident light and $l(\vec{x}, t)$ represents the intensity of the incident light. The time-dependent diffuse reflection can be represented as:

$$b(\lambda, \vec{x}, t) = v(\vec{x}, t) b_{DC}(\lambda, t) + \Delta v(\vec{x}, t) b_{AC}(\lambda, t),$$

where v represents the volume of static (no-pulse) blood, $\Delta v$ represents the volume of pulsatile blood; $b_{DC}(\lambda, t)$ represents the reflectance of static blood; and $b_{AC}(\lambda, t)$ represents the reflectance of pulsatile blood.

In the ratio-of-ratio technique, the effect of light intensity can be removed from the light response by:

$$\hat{R}_c(t) = \frac{I(\vec{x}, t)\sum_{\lambda_c} \hat{L}(\lambda) r_c(\lambda) m(\lambda, \vec{x}) \Delta v(\vec{x}, t) b_{AC}(\lambda, t)}{I(\vec{x}, t)\sum_{\lambda_c} \hat{L}(\lambda) r_c(\lambda) m(\lambda, \vec{x}) v(\vec{x}, t) b_{AC}(\lambda, t)},$$

which can be rewritten as:

$$\hat{R}_c(t) = \frac{\Delta v(\vec{x}, t)}{v(\vec{x}, t)} \frac{\sum_{\lambda_c} \hat{L}(\lambda) r_c(\lambda) m(\lambda, \vec{x}) b_{AC}(\lambda, t)}{\sum_{\lambda_c} \hat{L}(\lambda) r_c(\lambda) m(\lambda, \vec{x}) b_{AC}(\lambda, t)},$$

The dependency on blood volume can be eliminated by:

$$S(t) = \frac{\sum_{\lambda_1} \hat{L}(\lambda) r_c(\lambda) m(\lambda, \vec{x}) b_{AC}(\lambda, t)}{\sum_{\lambda_1} \hat{L}(\lambda) r_c(\lambda) m(\lambda, \vec{x}) b_{DC}(\lambda, t)} \frac{\sum_{\lambda_2} \hat{L}(\lambda) r_c(\lambda) m(\lambda, \vec{x}) b_{DC}(\lambda, t)}{\sum_{\lambda_2} \hat{L}(\lambda) r_c(\lambda) m(\lambda, \vec{x}) b_{AC}(\lambda, t)}$$

which can be rewritten as:

$$S(t) = \frac{AC_1/DC_1}{AC_2/DC_2},$$

where AC and DC refer to the pulsatile elements and non-pulsatile elements of the signal, at their respective subscripted wavelengths. As discussed more fully herein, S(t) is only related to blood reflectance if specular reflection is spatially invariant across the measured sample, i.e., if $$m(\lambda, \vec{x}) = m(\lambda).$$

In practice, unaccounted-for variations in the components of $R_c$ decrease the ability of the ratio-of-ratios technique to accurately reflect SpO2. For example, variations in ambient light will affect the incident light term $L(\lambda, \vec{x}, t)$, and if these variations are not controlled for, then changes in ambient light will erroneously appear as variations in a person's SpO2 measurements. A contactless, non-invasive SpO2 monitoring system should be robust to changes in ambient light so that a user can make accurate SpO2 measurements under different lighting conditions (e.g., at different times of the day, in different rooms or different locations within rooms, with different lights turned on or off, etc.) without having to meticulously control for ambient lighting conditions.

As another example, variations in the specular reflectance of a user's skin affects the light reflectance term $s(\lambda, \vec{x}, t)$. Variations in specular reflectance occur due to variations in skin components that affect the absorption of light in skin. For instance, the volume fraction of melanosomes in a person's epidermis may vary from 1% in paler skin to 5% in darker skin, and these variations can contribute significantly to the degree of light scatter within the epidermis. Other spatially varying reflectance properties due to variations in skin tissues can be due to variations in the presence of hair, the color and thickness variations in the user's skin, the presence of "blemishes" such as moles, etc. The variations in skin components alter the relationship between reflected light and the proportion of oxygenated hemoglobin, and therefore pose significant challenges to accurately estimating SpO2 using contactless approaches.

Figure 2:
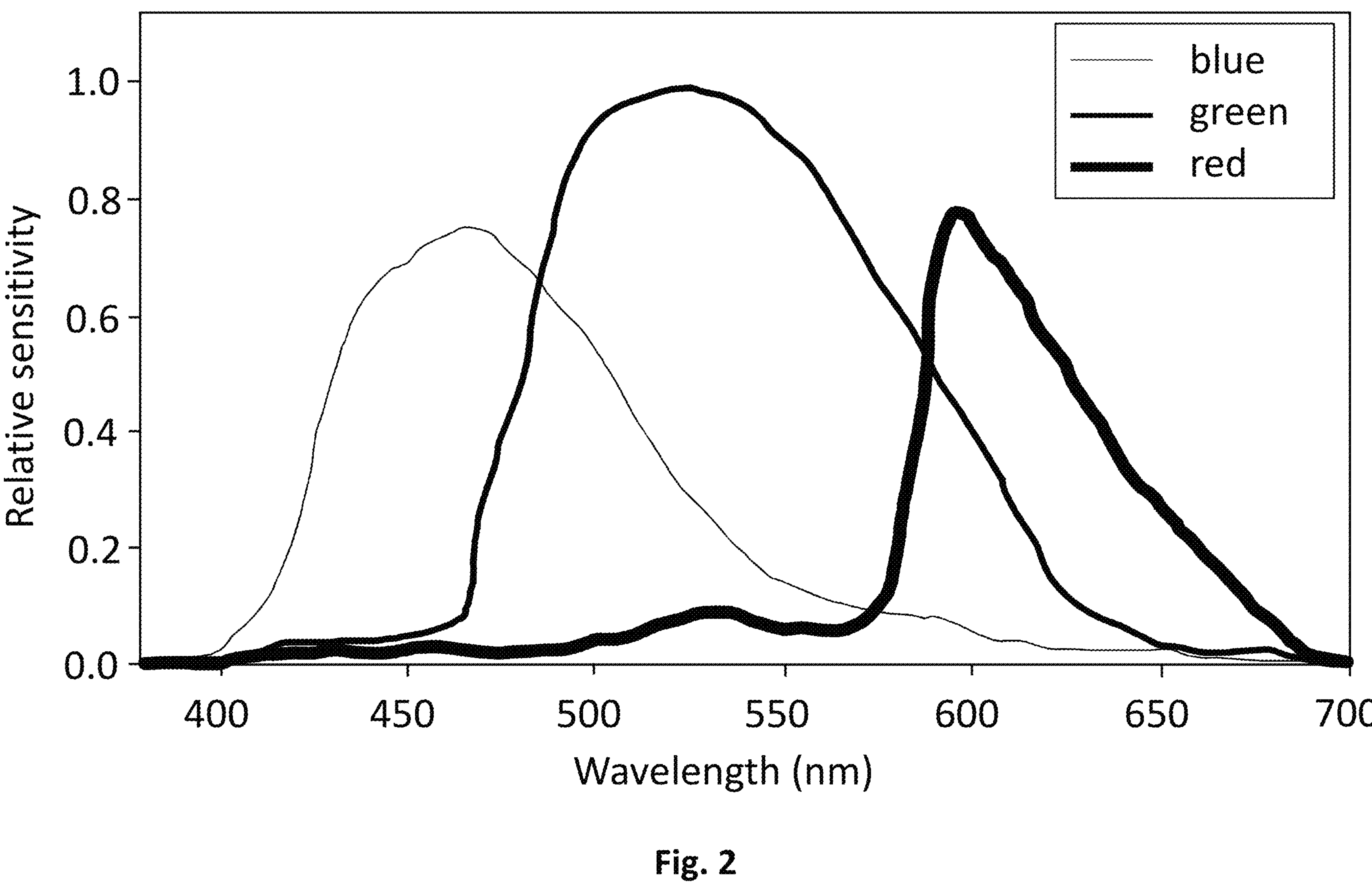
FIG. 2 illustrates an example response of an example smartphone camera's red, green, and blue sensors.

As another example, the ratio-of-ratios technique assumes that a sensor (e.g., camera) can independently detect two different wavelengths of light. For example, a finger pulse oximeter uses specialized sensors that detect red light and IR light, respectively, and the sensitive ranges of these sensors do not overlap. However, consumer cameras do not meet this requirement for RGB channels, as the camera response in different color channels (e.g., different wavelengths or ranges of wavelengths) overlaps between channels. For example, FIG. 2 illustrates an example response of an example smartphone camera's red, green, and blue sensors. As illustrated in FIG. 2, the camera sensor response in the blue channel overlaps with the sensor response in the green channel, etc., and an rPPG signal associated with this wide-band spectra creates complicated nonlinearity for SpO2 mappings, making the ratio-of-ratio technique unsuitable for estimating SpO2. In general, extracted RoR values depend on the configuration of a camera's sensor, which vary in their color spectral responses and their color filter arrays, meaning that two different cameras can have different sensor responses $r_c(\lambda, t)$ to the same lighting inputs. With different cameras, the same number of photons reflected from the skin may be perceived and converted to different electrical levels and digital values; if these differences are not controlled for, then they will erroneously appear as variations in estimated SpO2 values. Therefore, to deploy the SpO2 detection system on a new camera, careful factory calibration is needed by re-collecting, for each type of camera, large-scale subject's data during full range oxygen desaturation. This is time-consuming and very resource intensive.

Figure 3:
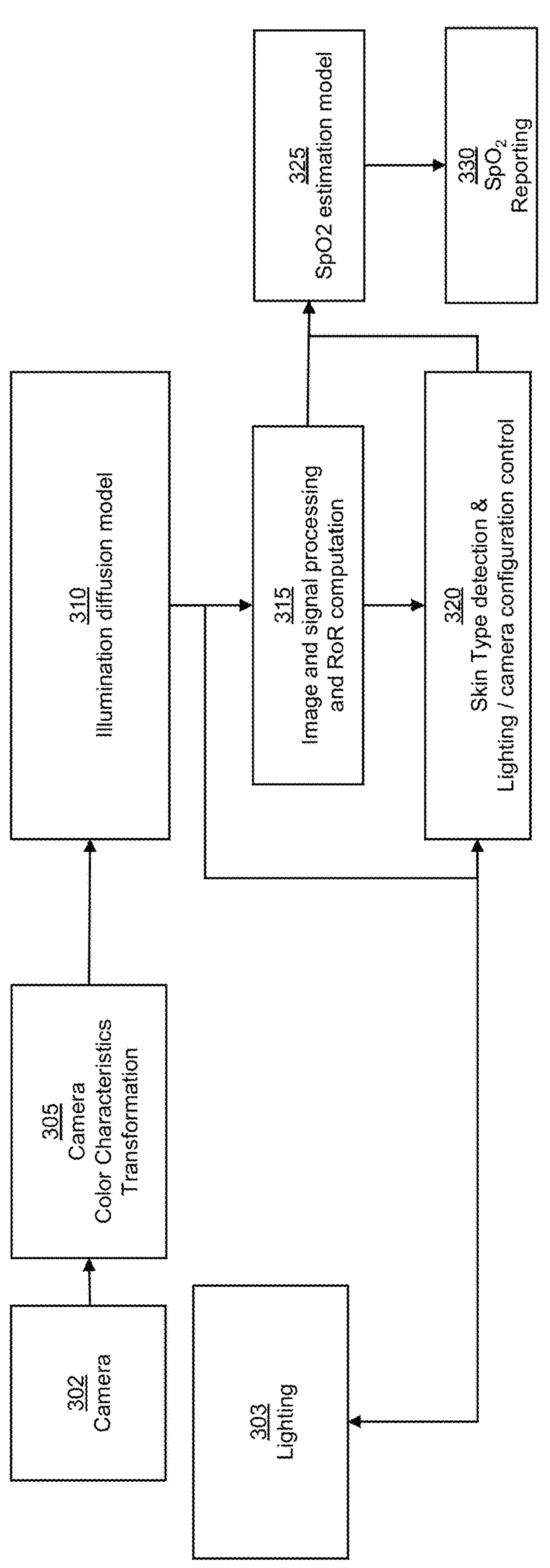
FIG. 3 illustrates an example architecture that improves contactless SpO2 detection by controlling for variations in ambient lighting, camera characteristics, and light-skin interactions across subjects.

FIG. 3 illustrates an example architecture that improves contactless SpO2 detection by compensating for variations in ambient lighting, camera characteristics, and light-skin interactions across subjects. While FIG. 3 illustrates an example architecture that eliminates or reduces the effects of each of these variations, particular embodiments of this disclosure may control for less than all three of these sources of variability for contactless SpO2 detection.

Figure 4:
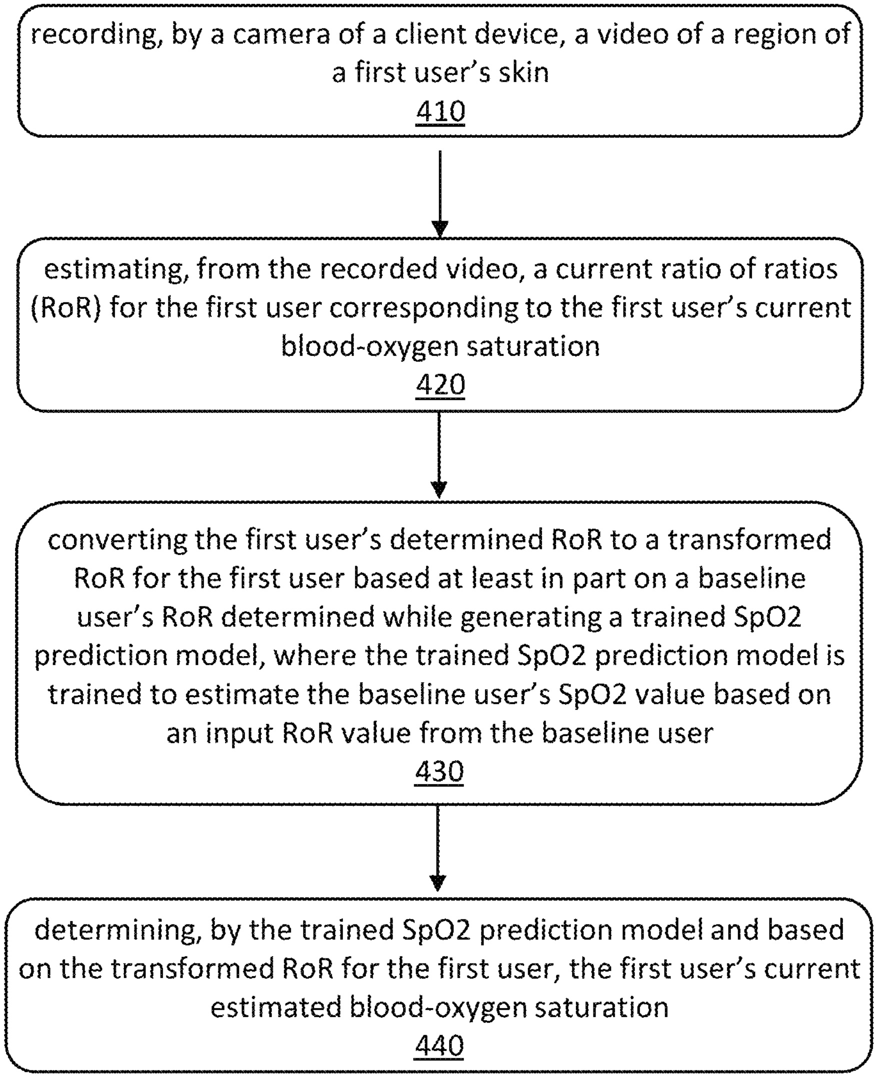
FIG. 4 illustrates an example method that compensates for the variability in light-skin interactions when performing contactless SpO2 detection.

FIG. 4 illustrates an example method that compensates for the variability in light-skin interactions when performing contactless SpO2 detection. Step 410 of the example method of FIG. 4 includes recording, by a camera of a client device, a video of a region of a first user's skin. The camera, such as camera 302 of the example architecture of FIG. 3, can be any camera, such as a camera of a smartphone, web camera, personal computer, tablet, wearable device, security camera, or other integrated or standalone camera. In particular embodiments, more than one camera may be used to capture video of a region of the first user's skin. Here, the video is a sequence of images captured by the camera. The region of skin can be any suitable visible region of skin and is often some or all of the user's face, but this disclosure contemplates that other regions of skin may be used alternatively or in addition to a user's face.

The camera captures images due to light reflections from the region of the first user's skin. The light reflections depend on the lighting present in the environment, e.g. lighting 303 in the example of FIG. 3. The lighting can include natural light, light from dedicated light sources (e.g., lamps, overhead lighting, etc.), and light from electronic devices (e.g., light from a display screen of a TV, smartphone, tablet, wearable, etc.), among other sources. Step 420 of the example method of FIG. 4 includes estimating, from the recorded video, a current ratio of ratios (RoR) for the first user corresponding to the first user's current blood-oxygen saturation. The captured video is processed to estimate the first user's current RoR; in the example of FIG. 3, this process occurs in block 315. This disclosure contemplates that any suitable approach for estimating RoR values from images of skin regions may be used, for example but not limited to the techniques described in U.S. patent application Ser. No. 18/213,461, and that description is incorporated herein by reference. A user's RoR values are related to their blood-oxygen saturation, but as discussed above, the exact relationship $f_{(RoR)} \rightarrow SpO2$ between RoR values and blood-oxygen saturation is not precisely uniform among different users, even when controlling for lighting and camera setting, because varying skin characteristics will affect how light at the relevant wavelengths for determining RoR is reflected from a person's skin.

Figure 5:
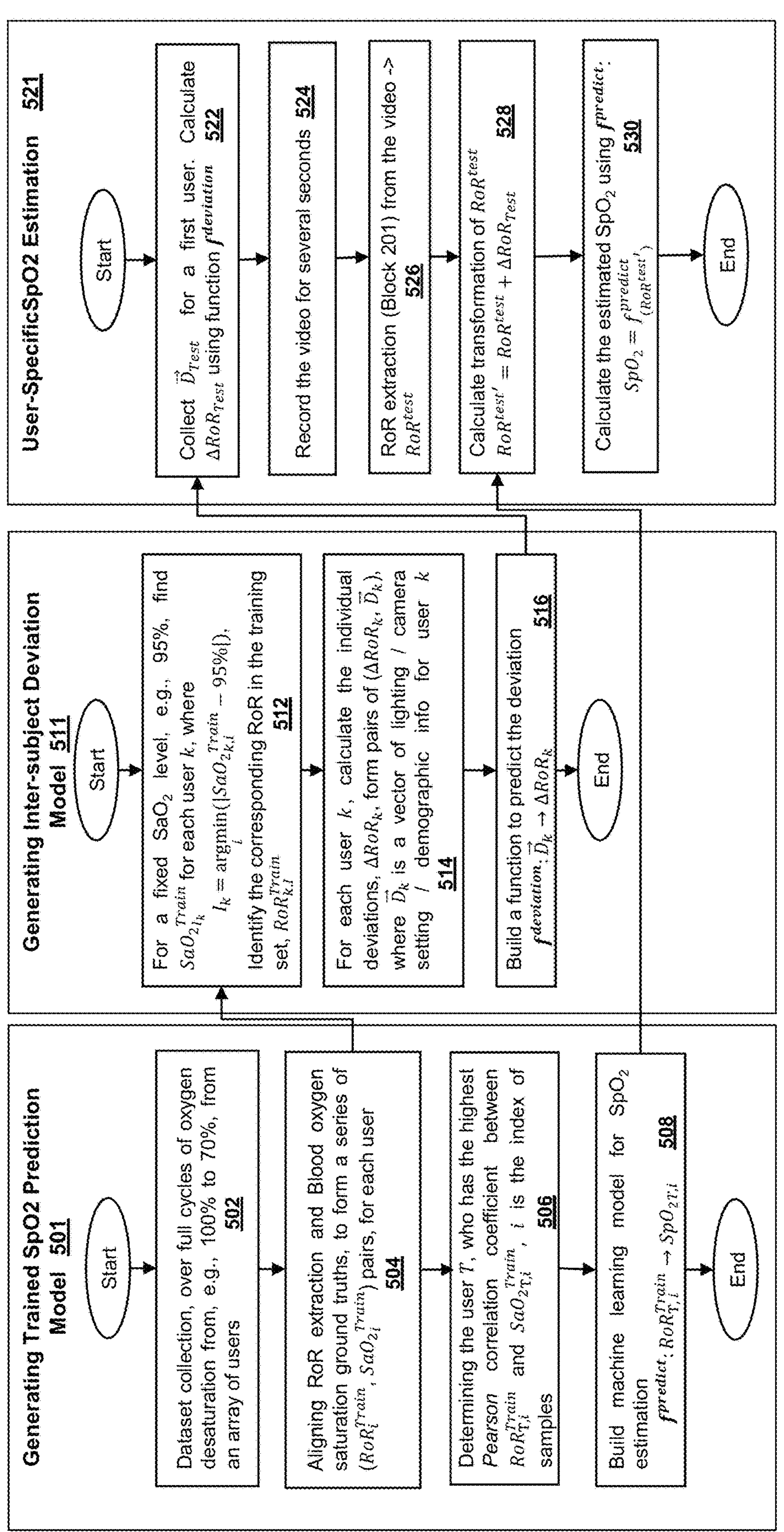
FIG. 5 illustrates a specific example implementation of steps 430 and 440 of FIG. 4.
Figure 6:
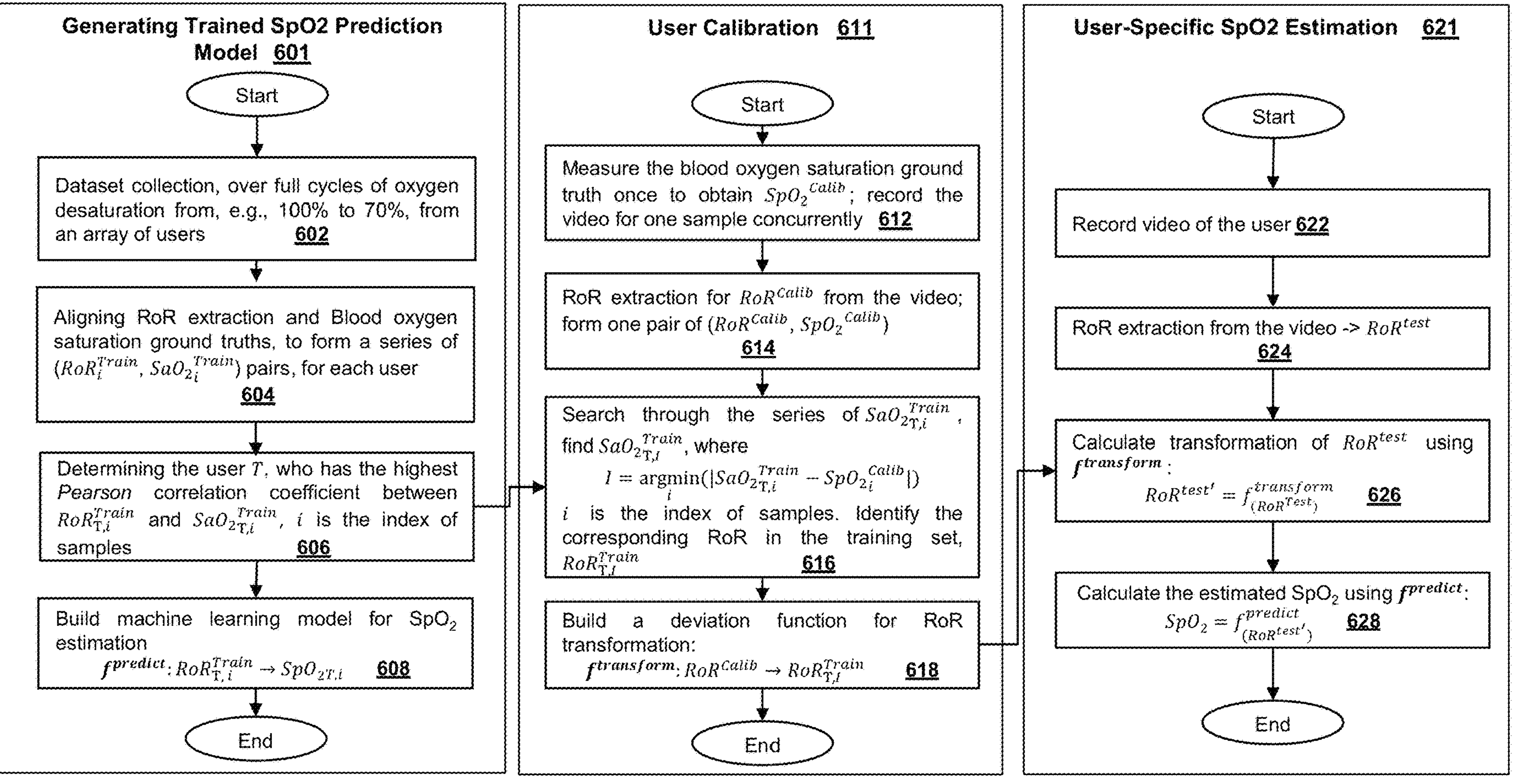
FIG. 6 illustrates a specific example implementation of steps 430 and 440 of FIG. 4.
Figure 7:
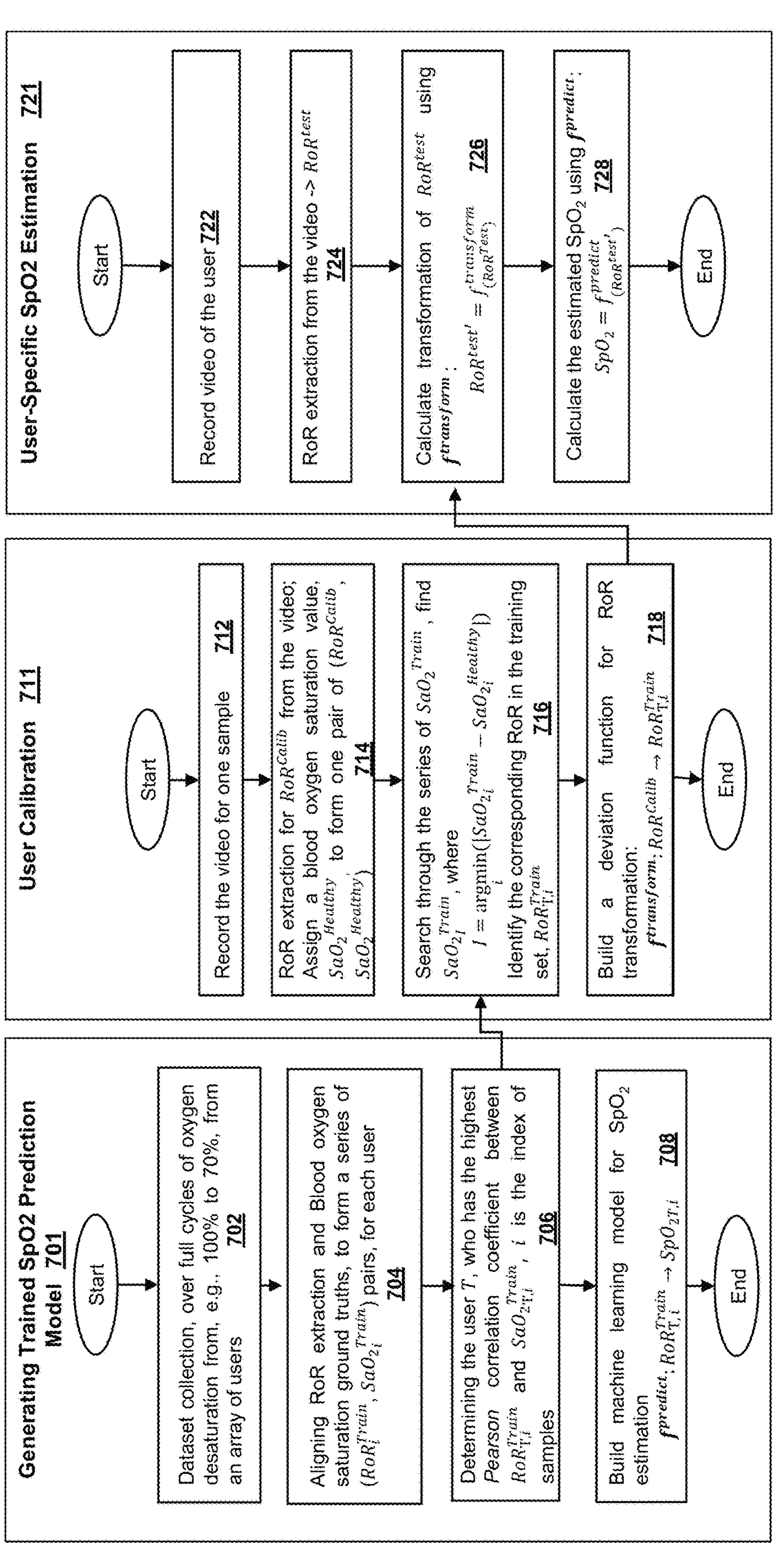
FIG. 7 illustrates a specific example implementation of steps 430 and 440 of FIG. 4.

Step 430 of the example method of FIG. 4 includes converting the first user's determined RoR to a transformed RoR for the first user based at least in part on a baseline user's RoR determined while generating a trained SpO2 prediction model, where the trained SpO2 prediction model is trained to estimate the baseline user's SpO2 value based on an input RoR value from the baseline user. Step 440 of the example method of FIG. 4 includes determining, by the trained SpO2 prediction model and based on the transformed RoR for the first user, the first user's current estimated blood-oxygen saturation. FIGS. 5-7 and the corresponding descriptions below provide detailed examples of specific embodiments of steps 430 and 440. In the example architecture of FIG. 3, these steps may be performed by block 325 to determine a user's current SpO2 value while reducing the errors caused by variations in light-skin interactions among different persons. As illustrated by block 330 in the example architecture of FIG. 3, the determined SpO2 values may be reported, for example to a user (e.g., via a display of a client device), to an electronic device (e.g., a client or server device tracking the user's SpO2 values) and/or to a medical professional (e.g., for health monitoring or during a telehealth visit).

FIG. 5 illustrates a specific example implementation of steps 430 and 440, and also describes corresponding example processes for generating a trained SpO2 prediction model and for generating the transformed RoR for the first user.

The example implementation of FIG. 5 includes a process 501 for generating a trained SpO2 prediction model. Step 502 of process 501 includes a dataset collection of blood-oxygen saturation values, over full cycles of oxygen desaturation from, e.g., 100% to 70%, from an array of n users. Step 502, like the rest of process 501, occurs prior to runtime SpO2 estimation for a user (e.g., prior to process 521). Steps of process 501 may be performed in, for example, a lab environment, and n may be a relatively large number. At this step, the blood-oxygen saturation values are determined using a ground-truth approach, such as for example using a pulse oximeter or an arterial blood gas test.

Step 504 of process 501 includes aligning RoR extraction and blood-oxygen saturation ground truths, to form a series of $$\left(RoR_i^{Train}, SaO2_i^{Train}\right)$$

pairs, for each of the n users. For instance, the RoR extraction may be performed according to the techniques of block 315 of the example architecture of FIG. 3. While $$SaO2_i^{Train}$$

may specifically refer to oxygen saturation of arterial blood as measured by an arterial blood gas test, here $$SaO2_i^{Train}$$

more generally refers to ground-truth oxygen saturation values, whether represented as $SaO_2$ as $SpO_2$.

Step 506 of process 501 includes selecting a particular user from the n users to subsequently use to train the SpO2 model. In this example, step 506 includes determining the user T who has the highest Pearson correlation coefficient between $$RoR_{T,i}^{Train} \text{ and } SaO2_{T,i}^{Train},$$

where i is the index of samples for the user T. While the example of FIG. 5 uses the Pearson correlation coefficient to select the user T from the n users, this disclosure contemplates that other metrics may be used to make this selection, with the purpose being to select a user that represents the strong predictive relationship between RoR and blood oxygenation values.

Once the user T is determined, then step 508 of process 501 includes generating the machine learning model for $SpO_2$ estimation:

$$f^{predict}: RoR_{T,i}^{Train} \rightarrow SpO2_{T,i}.$$

In other words, the model $f^{predict}$ is trained on user T's RoR and ground-truth oxygenation pairs until the model is sufficiently trained to predict SpO2 values for user T from T's input RoR values. Any suitable training condition(s) may be used, such as a number of iterations, an amount of time, a convergence of an objective function, and so on. The model $f^{predict}$ may be a deep-learning architecture, such as a neural network, but any suitable machine-learning model may be used, as the techniques described herein are not tied to any particular architecture for the model $f^{predict}$.

In the example of FIG. 5, after an SpO2 prediction mode $f^{predict}$ is generated in process 501, then process 511 may be used to generate a model $f^{deviation}$ for converting subsequent users' RoR values to corresponding RoR values obtained from the user T. Process 511 involves k users, which may be some, all, or none of the n users during process 501. Like process 501, process 511 occurs prior to real-time SpO2 estimation process 521, and the steps of process 511 may be performed in a laboratory setting.

Step 512 of the process 511 includes, for a fixed $SaO_2$ level, e.g., 95%, $$SaO_{2_{I_k}}^{Train}$$

for each user k, $$\text{where } I_k = \underset{i}{\text{argmin}}\left(\left|SaO_{2_{k,i}}^{Train} - \text{fixed } SaO2 \text{ level}\right|\right)$$

In other words, step 512 includes finding the $SaO_2$ value and corresponding index i that is nearest the fixed $SaO_2$ level, e.g., 95%, for each of the k users. Once that $SaO_2$ value and corresponding index is found for a particular user k, then step 512 includes identifying, for that user k, the RoR value in the training set $$RoR_{k,I}^{Train}$$

that corresponds to the identified blood-oxygenation value $$SaO_{2_{k,i}}^{Train}.$$

Step 514 of the process 511 includes, for each user k, calculating the individual deviations $\Delta RoR_k$ between the RoR value $$RoR_{k,I}^{Train}$$

for that user and the corresponding RoR value for the user T, $$RoR_{T,I}^{Train}.$$

In particular embodiments, $$\Delta RoR_k = RoR_{k,I}^{Train} - RoR_{T,I}^{Train}.$$

In other embodiments $$\Delta RoR_k = \frac{RoR_{I_k}^{Train}}{RoR_{I_T}^{Train}}.$$

Step 514 further includes forming pairs of ($\Delta RoR_k$, $\vec{D}_k$) for each user, where $\vec{D}_k$ is a vector of encodings of deviation-related parameters for that user at the time the user's data was captured. The deviation parameters may include lighting parameters, camera settings, and/or demographic information for that use. For example, demographic information may include one or more of the user's gender, age, BMI, and skin type. Lighting parameters may include or more of light intensity on a region of the user's skin (e.g., the forehead) and color temperature. Camera parameters may include one or more of camera white balance, gain, and exposure time.

Once the pairs ($\Delta RoR_k$, $\vec{D}_k$) from the k users are obtained, then step 516 of process 511 includes creating a function to predict the deviation $f^{deviation}$: $\vec{D}_k \rightarrow \Delta RoR_k$ from these pairs. In other words, the pairs are used to build the function $f^{deviation}$ that predicts, for a given user, a deviation in that user's RoR value from a baselines user's RoR value, given that user's deviation-related parameter vector DR. The function $f^{deviation}$ may be a machine-learning model (e.g., a neural network) or may be any other suitable functional approach.

Once the machine-learning model $f^{predict}$ and the deviation function $f^{deviation}$ are obtained, then these models can be used to transform a user's RoR values in real time for performing contactless SpO2 estimation. Process 521 illustrates one example process. Step 522 of process 521 includes collecting a deviation vector $\vec{D}_{Test}$ for a user. Step 521 may be performed once (e.g., the first time a user is onboarded to the system) or may be performed periodically (e.g., at certain time intervals, when the user's demographics are predicated to have changed, when the user inputs new demographic information, etc.). The deviation vector $\vec{D}_{Test}$ may be obtained from user input or may be obtained automatically (e.g., by automatically measuring the user's BMI, gender, etc.). Once the deviation vector $\vec{D}_{Test}$ is obtained for a particular user, then the RoR deviation $\Delta RoR_{Test}$ from the baseline user T can be predicted for user by the function $f^{deviation}$ i.e., by providing the vector $\vec{D}_{Test}$ to the trained function $f^{deviation}$, which outputs the predicted RoR deviation $\Delta RoR_{Test}$.

Step 524 of process 521 includes using a camera to record a video of the user for a certain length of time, e.g., several seconds. This step corresponds to step 410 of the example method of FIG. 4. Step 526 of process 521 includes estimating the RoR of the user from the video, for example, by using the techniques described in connection with block 315 of FIG. 3. This estimated RoR is designated by $RoR^{test}$, and this estimation process corresponds to step 420 of the example method of FIG. 4. Then step 528 of process 521 includes calculating the transformation of $RoR^{test}$ to an RoR value, $RoR^{test'}$, that will result in meaningful SpO2 prediction from $f^{predict}$. For example, in particular embodiments, $RoR^{test'} = RoR^{test} + \Delta RoR_{Test}$, while in other embodiments, $RoR^{test'} = RoR^{test} / \Delta RoR_{Test}$, depending on whether $f^{deviation}$ predicts ΔRoR as a difference from a baseline user or as a ratio relative to a baseline user. Step 528 of process 521 is one example of step 430 of the example method of FIG. 4. Step 530 of process 521 includes calculating the estimated $SpO_2$ using $f^{predict}$ with $RoR^{test'}$ (not $RoR^{test}$) as the input. Here, step 530 is one example of step 440 of the example method of FIG. 4.

As explained above, contactless SpO2 estimates can be erroneously affected by variations in ambient lighting, camera settings, and users' skin characteristics. The process of FIG. 5 controls for one or more of these variations via: (1) deviation vector $\vec{D}_{Test}$ specific to particular user, (2) $f^{deviation}$ trained to estimate how a user-specific deviation vector affects that user's measured RoR values relative to a baseline user, and (3) $f^{predict}$, which estimates SpO2 values based on input RoR values for the baseline user. In effect, during process 521 a first user's measured RoR value is converted (using the first user's lighting, camera, and/or demographic information) to a transformed RoR value that would correspond to a baseline user's RoR value, and then this transformed RoR value is used to estimate an SpO2 value for the first user, even though the model $f^{predict}$ was trained off of the baseline user's values. As a result, many different first users' SpO2 values can be predicted without having to train a model $f^{predict}$ for each user, which would be impractical and extremely resource intensive. Instead, using the techniques described in connection with FIG. 5, a model $f^{predict}$ can be built for one baseline user, and yet that model can be used to accurately predict SpO2 values for other users under varying lighting, camera, and/or skin conditions.

Either or both of models $f^{predict}$ and $f^{deviation}$ may be deployed on a server device or a device local to the first user in process 521. For example, process 521 may be performed on a local device, or a local device may transmit data to another device (e.g., a server device) hosting one or both of $f^{predict}$ and $f^{deviation}$, which may then transmit the resulting output back to the local device.

While in the example of FIG. 5 a user provides demographic information, either manually or during an automated detection phase, no specific user calibration of lighting equipment, camera equipment, or RoR or SpO2 estimation models is required. In addition, no assumptions are made as to any specific user's health, and the resulting SpO2 estimation has high accuracy. However, a large-scale training dataset is required to generate $f^{predict}$ and $f^{deviation}$.

FIG. 6 illustrates another specific example implementation of steps 430 and 440, and also describes corresponding example processes for generating a trained SpO2 prediction model and for generating the transformed RoR for the first user.

The example implementation of FIG. 6 includes a process 601 for generating a trained SpO2 prediction model. Process 601 is analogous to process 501, and the description of process 501 and of steps 502, 504, 506, and 508 applies to process 601 and steps 602, 604, 606, and 608, respectively. In particular embodiments, process 501 and 601 may be the same, in that process 501 serves as a dataset for deployments using the example of FIG. 5 and for deployments using the example of FIG. 6.

User calibration process 611 is a calibration process specific to each user. Step 612 includes measuring the user's ground-truth SpO2 values while, at the same time, recording a sample of video of a region of the user's skin. A sample of video may be, e.g., a few seconds worth of video. Then, at step 614, the user's RoR is extracted from the video sample (e.g., using the techniques described in connection with block 315 of FIG. 3) to form a RoR-SpO2 pair $$\left(RoR^{Calib}, SpO_2^{Calib}\right).$$

Step 616 includes searching through the series, obtained during process 601, of $$SaO_{2_{T,i}}^{Train},$$

to find $$SaO_{2_{T,I}}^{Train},$$

where $$I = \underset{i}{\operatorname{argmin}}\left(\left|SaO_{2_{T,i}}^{Train} - SpO_{2_i}^{Calib}\right|\right).$$

In other words, the user's ground-truth SpO2 value is obtained in step 614, and then the baseline user T's closest SaO2 value is found from the index of user T's SaO2 samples. Once $$SaO_{2_{T,i}}^{Train}$$

is found, then the corresponding RoR value for user T is found, i.e., $$RoR_{T,I}^{Train}.$$

Step 618 includes making a deviation function, or transformation function, for converting RoR from the calibration user (the first user) to the baseline user. The transformation function is represented as $$f^{transform}: RoR^{Calib} \rightarrow RoR_{T,I}^{Train}.$$

For instance, in particular embodiments $$f_{\left(RoR^{Calib}\right)}^{transform} = RoR^{Calib} + \Delta RoR, \text{ where } \Delta RoR = RoR_{T,I}^{Train} - RoR^{Calib}.$$

As another example, in particular embodiments, $$f_{\left(RoR^{Calib}\right)}^{transform} = RoR^{Calib} \times \Delta RoR, \text{ where } \Delta RoR = RoR_{T,I}^{Train} / RoR^{Calib}.$$

Once the transformation function is obtained for a specific first user in process 611, then a user-specific SpO2 estimation process 621 can be performed for that user. Step 622 of process 621 includes recording video of the user, e.g., for several seconds. Step 624 includes estimating a current RoR $RoR^{test}$ for the user from the video (e.g., using the RoR estimation techniques described in connection with block 315 of FIG. 3). Step 626 of FIG. 6 includes transforming $RoR^{test}$ for the first user to a corresponding RoR value of the baseline user, using $f^{transform}$ for the first user, so that $$RoR^{test'} = f_{\left(RoR^{Test}\right)}^{transform}.$$

Then, the first user's current SpO2 value can be estimated using $RoR^{test'}$ and the $SpO_2$ estimation model built for the baseline user in process 601, i.e., $f^{predict}$. Step 626 is one example of step 430 of the example method of FIG. 4, and step 628 of FIG. 6 is one example of step 440 of the example method of FIG. 4. In general, $f^{predict}$ and $f^{transform}$ may be deployed on a server device or on a device local to the first user (e.g., on a smartphone of the first user).

Compared to the example of FIG. 5, the example of FIG. 6 requires more user engagement, in that a user calibration phase 611 is required, but this user engagement is relatively minimal, as step 611 may be performed only once, or may be performed periodically; but in any event, process 611 is not performed before every contactless SpO2 estimation of process 621. The approach of FIG. 6 doesn't require a large-scale data collection to train a deviation model $f^{deviation}$, therefore reducing the resources required to deploy the example of FIG. 6. In addition, the approach of FIG. 6 doesn't make any assumptions about a user's health conditions, and it results in fairly high accuracy in SpO2 estimation.

FIG. 7 illustrates another specific example implementation of steps 430 and 440, and also describes corresponding example processes for generating a trained SpO2 prediction model and for generating the transformed RoR for the first user.

The example implementation of FIG. 7 includes a process 701 for generating a trained SpO2 prediction model. Process 701 is analogous to process 501 (and 601), and the description of process 501 and of steps 502, 504, 506, and 508 applies to process 701 and steps 702, 704, 706, and 708, respectively. In particular embodiments, process 501 and 701 may be the same, in that process 501 serves as a dataset for deployments using the example of FIG. 5 and for deployments using the example of FIG. 7 (as well as, in particular embodiments, the deployments using the example of FIG. 6).

User calibration process 711 is a calibration process specific to each user. Step 712 includes obtaining a sample of video of a region of the user's skin. A sample of video may be, e.g., a few seconds worth of video. Then, at step 714, the user's RoR is extracted from the video sample (e.g., using the techniques described in connection with block 315 of FIG. 3). Step 714 also include assigning the user an SaO2 value, e.g., $$SaO_2^{Healthy},$$

to form one pair of $$\left(RoR^{Calib},\ SaO_2^{Healthy}\right)$$

for the user. The assigned SaO2 value may be based on user-specific data such as the user's altitude, age, and body mass. For example, in particular embodiments $$SaO_2^{Healthy} = 97\%$$

between sea level and 5,000 ft in altitude, while $$SaO_2^{Healthy} = 95\%$$

above 5,000 ft. in altitude.

Step 714 includes searching through the series, obtained during process 701, of $$SaO_{2_{T,i}}^{Train},\ \text{to find}\ SaO_{2_{T,I}}^{Train},$$

where $$I = \underset{i}{\operatorname{argmin}}\left(\left|SaO_{2_{T,i}}^{Train} - SaO_{2_i}^{Healthy}\right|\right).$$

In other words, the user's assigned SaO2 value is determined in step 714, and then the baseline user T's closest Train is found, then the SaO2 value is found from the index of user T's SaO2 samples. Once $$SaO_{2_{T,i}}^{Train}$$

is found, then the corresponding RoR value for user T is found, i.e., $$RoR_{T,I}^{Train}.$$

Step 718 is analogous to step 618, and includes making a deviation function, or transformation function, for converting RoR from the calibration user (the first user) and the baseline user. The transformation function is represented as $$f^{transform}\colon RoR^{Calib} \rightarrow RoR_{T,I}^{Train}.$$

For instance, in particular embodiments $$f_{\left(RoR^{Calib}\right)}^{transform} = RoR^{Calib} + \Delta RoR,\ \text{where}\ \Delta RoR = RoR_{T,I}^{Train} - RoR^{Calib}.$$

As another example, in particular embodiments, $$f_{\left(RoR^{Calib}\right)}^{transform} = RoR^{Calib} \times \Delta RoR,\ \text{where}\ \Delta RoR = RoR_{T,I}^{Train} / RoR^{Calib}.$$

Once the transformation function is obtained for a specific first user in process 711, then a user-specific SpO2 estimation process 721 can be performed for that user. Step 722 of process 721 includes recording video of the user, e.g., for several seconds. Step 724 includes estimating a current RoR $RoR^{test}$ for the user from the video (e.g., using the RoR estimation techniques described in connection with block 315 of FIG. 3.) Step 726 of FIG. 7 includes transforming $RoR^{test}$ for the first user to a corresponding RoR value of the baseline user, using $f^{transform}$ for the first user, so that $$RoR^{test'} = f_{\left(RoR^{Test}\right)}^{transform}.$$

Then, the first user's current $SpO_2$ value can be estimated using $RoR^{test'}$ and the $SpO_2$ estimation model built for the baseline user in process 701, i.e., $f^{predict}$. Step 726 is one example of step 430 of the example method of FIG. 4, and step 728 of FIG. 6 is one example of step 440 of the example method of FIG. 4. In general, $f^{predict}$ and $f^{transform}$ may be deployed on a server device or on a device local to the first user (e.g., on a smartphone of the first user).

The example of FIG. 7 requires very minimal user engagement, as no ground-truth SpO2 measurement is required. The approach of FIG. 7 also doesn't require a large-scale data collection to train a deviation model $f^{deviation}$, therefore reducing the resources required to deploy the example of FIG. 7. However, the approach of FIG. 7 assumes that a user is healthy, and therefore this approaches results in fairly high accuracy in SpO2 estimation if the user is actually healthy. In particular, although the approach of FIG. 7 may be relatively less accurate compared to FIGS. 5 and 6 in certain circumstances, this approach can still be effective in detecting desaturation events in the users' blood.

In can be particular challenging to accurately detect oxygen saturation using contactless methods for users with darker skin tones, e.g., as determined by the Fitzpatrick Skin Type scale, which relates to mean melanin content in a person's skin. Melanin largely governs skin tone, and in general, the concentration of melanin increases exponentially across Fitzpatrick skin types, and dramatically peaks at Skin Type VI. The major optical absorbers in tissue are melanin and oxy/deoxy-hemoglobin; and melanin absorbs light up to 20 times more than hemoglobin in the red color band, which introduces substantial interference in $SpO_2$ detection when using contactless methods.

Figure 8:
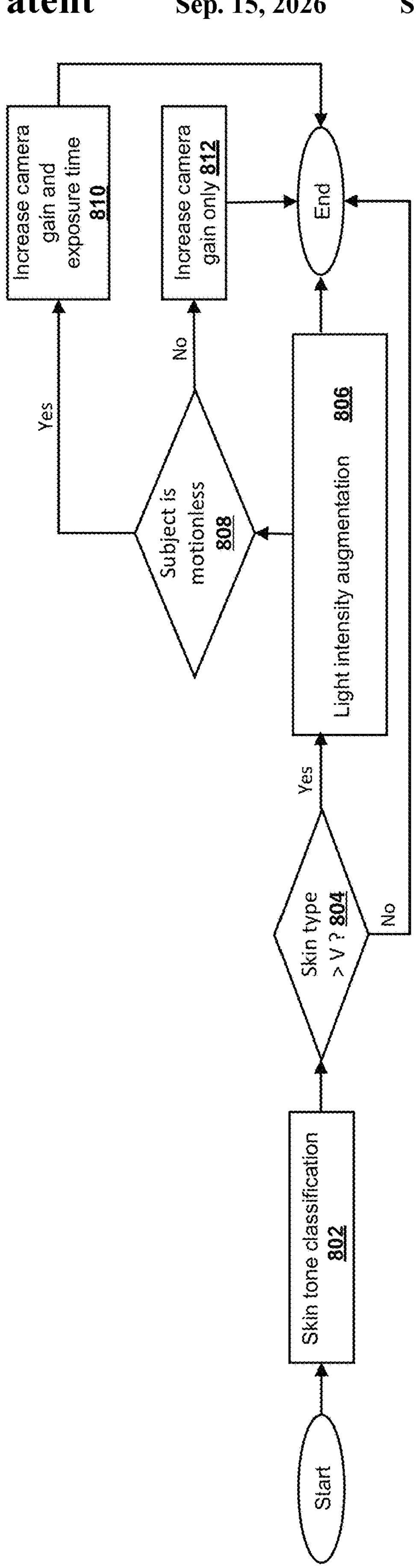
FIG. 8 illustrates an example approach used by block 320 of FIG. 3.

Particular embodiments of this disclosure include techniques to improve SpO2 detection accuracy for user's with relatively high melanin content. Block 320 of FIG. 3 illustrates an example approach for controlling aspects of lighting 303 to improve SpO2 accuracy in these instances. FIG. 8 illustrates an example approach used by block 320. First, in steps 802 and 804 the user's skin type is detected and classified, e.g., according to the Fitzpatrick Skin Type scale. If the user's skin type is not above threshold type, e.g., type V, then the process may end, and block 320 may not alter the SpO2 detection approach. If the classified skin type is above the threshold, then step 806 may perform a light intensity augmentation, for example by increasing the intensity of one or more lighting sources 303. For example, if a user's display screen is providing some of the lighting 303, then step 806 may include increasing the intensity or brightness of the display screen, thereby increasing the light incident on the user. If the system is connected to other lighting sources, such as a smart lighting system, then step 806 may include increasing the intensity of one or more of these lighting sources.

As illustrated in FIG. 8, particular embodiments may use a motion detection decision 808 to determine whether a subject is relatively motionless while capturing video for SpO2 estimation. If yes, then at step 810, in addition to augmenting the lighting both the gain setting and exposure time of the camera capturing the video may be increased. If the user is not sufficiently motionless, then only the camera's gain may be increased in step 812.

In particular embodiments, the output of skin-type detection block may also be used to select a SpO2 estimation model, e.g., in FIG. 3, the output of block 320 may be used to select a model to use in block 325. For example, if the user's skin type is greater than a threshold, e.g., greater than type V, then block 325 may use an SpO2 prediction model built on data from subjects with at least that skin type. For instance, in the examples of FIGS. 5, 6, and 7, a model $f^{predictVI}$ may be selected, where $f^{predictVI}$ is trained from data specifically on subjects having skin type of at least VI.

Figure 9:
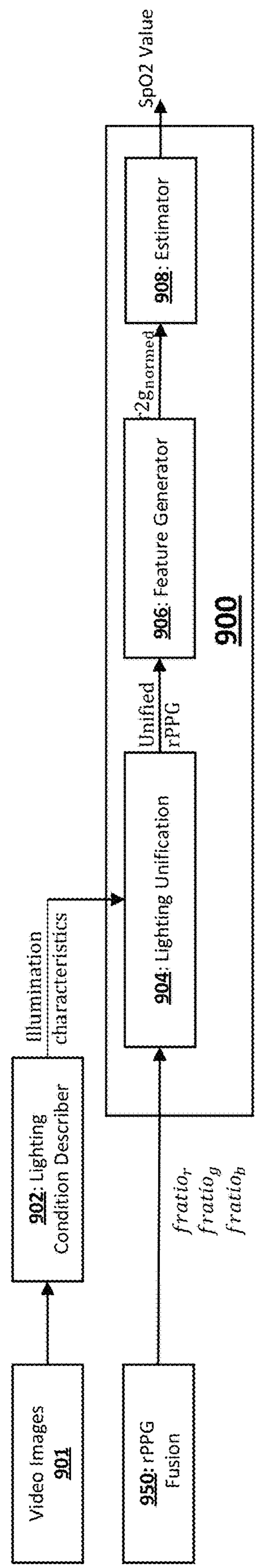
FIG. 9 illustrates an example architecture of an illumination diffusion model.

Particular embodiments may use an illumination diffusion model (e.g., block 310 in the example of FIG. 3) in order to adjust the illumination present in a recorded video to an improved illumination, thereby reducing the effects of illumination variability on estimated SpO2 values using contactless methods. FIG. 9 illustrates an example approach for an illumination diffusion model.

A Lighting Condition Describer Block 902 receives images 901 from video of the user's skin (e.g., videos of the user's face). Block 902 outputs illumination characteristics, for example by classifying the lighting conditions; e.g., classifying color temperature as warm, neutral, or cool. The characteristics output by block 902 are sent to the Lighting Unification Block 904. Block 904 normalizes the rPPG data, with its actual light condition, into a unified rPPG signal that represents what the signal would be under ideal light conditions; how block 904 achieves this is described in more detail below. Feature Generator Block 906 takes the output from Lighting Unification Block 904, to generate normalized RoR(s) ($r2g_{normed}$) from the rPPG signal with unified color condition, by dividing the fused ratio values from the respective colors. Feature generator block 906 may be the same feature generator block used when the lighting conditions are ideal, although the features output by this block may vary based on lighting conditions. The Normalization-based Estimator Block 908 takes the normalized RoR(s) to generate $SpO_2$ estimation values using, e.g., a machine learning model. As a result, blocks 900 and 902 correct for variations in lighting conditions in a particular dataset by adjusting the data to estimate how the data would have been captured had it been captured under ideal lighting conditions. In the example of FIG. 9, the rPPG signal output from rPPG fusion block 950 may be provided by any suitable technique, such as the techniques described in U.S. patent application Ser. No. 18/213,461, and such description is incorporated herein by reference.

In particular embodiments, block 904 may be a diffusion model that, in general, functions by deliberately introducing noise into training data and subsequently learning to reverse this process (i.e., learning to remove noise from the data it receives). A well-trained diffusion model can generate data from random noise by iteratively removing the predicted noise. Embeddings, such as text descriptions for image generation, can be added to guide the content generation process. In this disclosure, particular embodiments treat an input rPPG signal under different lighting conditions as the noisy signal. Such embodiments then recover rPPG signals under an ideal, controlled lighting, given the rPPG observation under different lighting conditions as the embedding. In particular embodiment, block 904 may contain a diffusion model trained on each color channel of the RGB signal. In other embodiments, block 904 may be a single diffusion model that may be used for each of all three channels.

For contactless SpO2 estimation, the information brought by the light source is bounded by the physical limitation of light absorption spectra of oxy- and deoxygenated hemoglobin for the wavelengths included in the light source. Warmer color temperature provides better discrimination power, in which scenario the red and green colors are sufficient to provide the estimation. However, under a cool color temperature, the light intensity is weaker in the red band. Therefore, particular embodiments treat the warm color temperature as the ideal lighting condition and the rPPG signal under warm color temperature as the training target. When block 904 receives the lighting conditions from block 902, then block 904 may determine whether the lighting conditions are equivalent to (or sufficiently equivalent to) the predetermined ideal lighting conditions. If yes, then block 904 does not need to do any further processing on the rPPG data (e.g., the lighting unification of block 904 in FIG. 9 can be bypassed). However, if the lighting conditions are not sufficiently equivalent to the ideal lighting, then block 904 can pass the rPPG data to a diffusion-based unifier to generate the output unified rPPG signals.

Warm lighting conditions achieve the best SpO2 estimation performance for contactless approaches because the computed features from the rPPG signals have the highest correlation with SpO2 values. Therefore, the rPPG signals under warm lighting condition are treated as the training target/label. rPPG signals obtained under different, non-warm lighting conditions (e.g., neutral and cool color temperature) are treated as the "noisy" version of the rPPG signal under warm color temperature; the rPPG signals under such sub-optimal illumination conditions show more fluctuations than the rPPG signal under warm color condition. The diffusion-based lighting unification model is trained to convert the "noisy" rPPG signal into the ideal rPPG signal (i.e. the rPPG signal as it would appear if obtained under the ideal lighting conditions). This process occurs for each color channel used in the SpO2 estimation process; e.g., if all three RGB color channels are used, then all three color channels will be corrected by the diffusion-based lighting unification model.

The diffusion-based unifier of block 904 may be trained by inputting ground truth pairs of rPPG signals under ideal lighting and non-ideal lighting, along with the lighting condition(s) describing the non-deal lighting. These pairs are based on images from the same camera and of the same subject, with only lighting conditions being modified. The unifier is trained based on a target loss between the modified rPPG signal under non-ideal lighting (i.e., the output of the diffusion model) and the ground-truth rPPG signal under ideal lighting.

Particular embodiments may correct for variations in characteristics of the camera used to capture video of a user for contactless SpO2 estimation. Block 305 of the example of FIG. 3 illustrates an example approach for addressing this inter-camera variability. As explained above, different color spectral responses and color filter arrays used by various cameras affect how light is converted to electronic signals. Therefore, even for a subject with a fixed blood oxygen saturation and a fixed surrounding illumination, two different cameras will likely result in two different detected signals in the RGB color channels, and therefore will result in different estimated RoR and SpO2 values. Calibrating a contactless SpO2 estimation model for every camera is extremely resource intensive, as this process takes costly and lengthy data collection and analysis procedure to train a SpO2 estimation model for a specific camera, including requiring dedicated lab settings and equipment, certified clinical professionals, large scale data collection and analysis, and several test subjects.

Particular embodiments address inter-camera variability by transforming the video color characteristics from a given camera to those of a benchmark camera. For instance, particular embodiments may use block 305 in example of FIG. 3 to convert color characteristics of the video received from camera 302 to video representing color characteristics as if captured by a benchmark camera. The SpO2 prediction model (e.g., block 325 of FIG. 3) can be trained using video from the benchmark camera, and therefore the converted video output by block 305 contains the color characteristics used to train the SpO2 prediction model. The predicted SpO2 will thus contain fewer (or no) artifacts as a result of mismatched color characteristics between the camera used to capture video and the camera used to capture the video on which the SpO2 model was trained.

Figure 10:
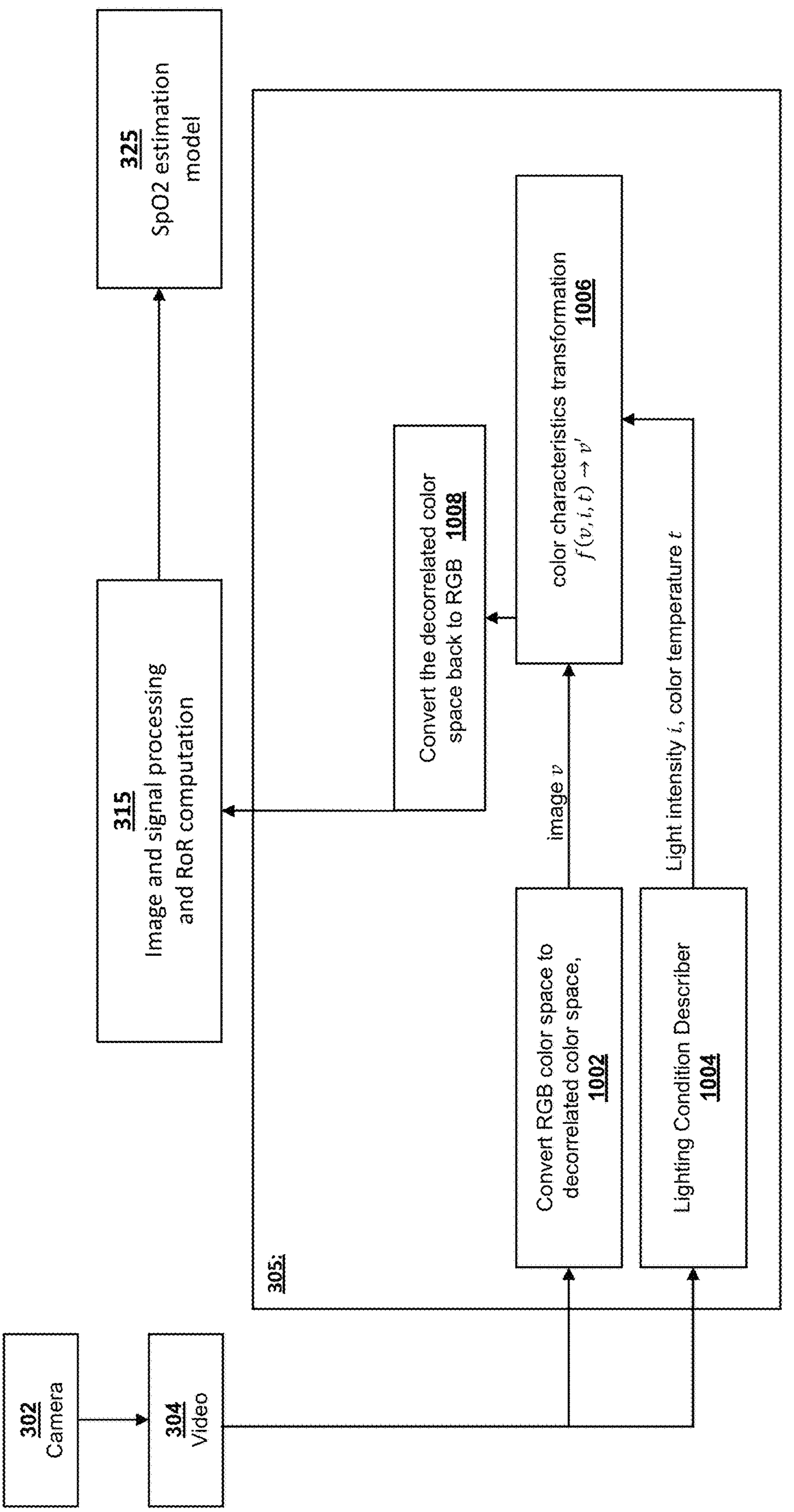
FIG. 10 illustrates an example of block 305 of FIG. 3.

FIG. 10 illustrates an example of block 305 of FIG. 3. Camera 302 captures video 304 of a first user, and this video is passed to block 305. Specifically, in the example embodiment of FIG. 10, video 304 is input to block 1002, which converts the RGB color space in the received video to a decorrelated color space, e.g., YUV or $l\alpha\beta$. The result of block 1002 operating on an image is output image v in the decorrelated color space. Video 304 is also input to block 1004, which describes the lighting conditions, for example, by using the techniques described in U.S. patent application Ser. No. 18/213,461, and such techniques are incorporated herein by reference. The output of block 1004 is a light intensity value i and a color temperature value t for the image. The outputs of blocks 1002 and 1004 are input to block 1006, which implements a color-characteristic transformation $f(v, i, t) \rightarrow v'$. In other words, block 1006 transforms image v having lighting conditions i and t to image v'. Transformed image v' is passed to block 1008, which converts v' from the decorrelated color space back to the RGB color space, and this image is then passed to block 315, which is described above. Thus, the example architecture of FIG. 10 controls for variation in camera parameters by transforming the images captured from camera 302 to images as if they were captured by the camera used to generate training video for the SpO2 estimation model of block 325.

To train block 1006, an array of paired images are captured. One set of images (e.g., of a person's face) are captured by a benchmark camera, with each image having a certain intensity and color temperature value (i.e., the benchmark camera captures images of the user's face across a range of color temperatures and intensities). Each new camera (e.g., a particular make/model of camera) captures the same images across the same intensity and color temperature ranges. For instance, the benchmark camera and a particular new camera may be collocated and synchronized to capture images at the same time. A computerized LED panel may be controlled to scan through the whole RGB color space and the dynamic range of the light intensity. One image from the benchmark camera, and one image from the new camera are captured under each of the color temperature, and light intensity. An autoencoder model is trained, using the array of image pairs as input, to learn a transfer function between the color characteristics of images captured by the new camera to the color characteristics of images captured by the benchmark camera. Both pairs of images are transformed to a decorrelated color space prior to being input to the autoencoder, as this decorrelation allows the three color channels to be processed independently of each other during the autoencoder's statistical correction process. In particular embodiments, the training images (as well as the images input to block 305 in FIG. 10) may be cropped, e.g., to the region of the user's skin that will be used to make RoR and SpO2 estimates.

In particular embodiments, a new SpO2 model may be trained for a particular camera from an existing, benchmark SpO2 model trained on images from a benchmark camera. For instance, the estimated spectral sensitivity of a new camera and the spectral sensitivity of benchmark camera may be input to a transfer function $f$ such that, given input video that was recorded from the benchmark camera, $f$ generates a synthesized video as if the video was recorded from the particular camera. The transfer function can be learned from the spectral sensitivity from both the benchmark camera and the particular camera, and these sensitivity parameters can be obtained from the camera manufacturers. Training videos are recorded for the benchmark camera, and these training videos, along with the output of the transfer function from a raw camera to the particular camera are used to determine the color characteristics transformation for the benchmark camera to the particular camera. This color characteristics transformation along with ground-truth SpO2 corresponding to the training videos are then use to generate the SpO2 estimation model (e.g., block 325 of FIG. 3) that is specific to the particular camera.

The techniques described herein may be used in a wide variety of use cases. For example, the techniques may be used to estimate a user's SpO2 values during a telehealth visit with a medical professional, and video of the user used for the telehealth visit may also be used to estimate the user's SpO2 values. As another example, the techniques described herein for contactless SpO2 estimation may be used while a user is using or facing a device, such as a TV, laptop, smartphone, etc., that has a camera facing the user, and therefore passive, contactless estimates of the user's SpO2 values may be made while the user is using the device or is otherwise engaged in other activities. For example, contactless SpO2 estimates may be made for a user while the user is watching TV, working at a computer, scrolling through content on her smartphone, exercising, etc. Cameras may also be deployed on, e.g., airplanes, cars, in hospitals, etc. for contactless SpO2 estimation of subjects in the field of view of the camera.

Figure 11:
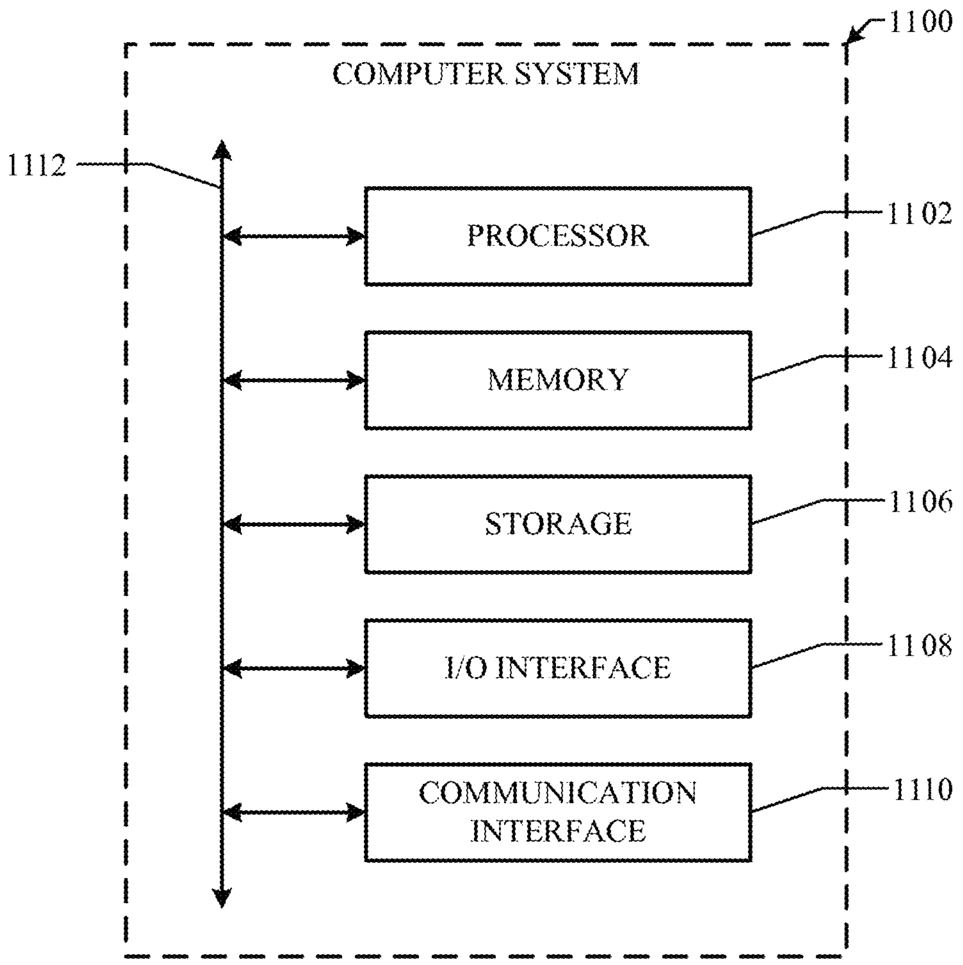
FIG. 11 illustrates an example computing system.

FIG. 11 illustrates an example computer system 1100. In particular embodiments, one or more computer systems 1100 perform one or more steps of one or more methods described or illustrated herein. In particular embodiments, one or more computer systems 1100 provide functionality described or illustrated herein. In particular embodiments, software running on one or more computer systems 1100 performs one or more steps of one or more methods described or illustrated herein or provides functionality described or illustrated herein. Particular embodiments include one or more portions of one or more computer systems 1100. Herein, reference to a computer system may encompass a computing device, and vice versa, where appropriate. Moreover, reference to a computer system may encompass one or more computer systems, where appropriate.

This disclosure contemplates any suitable number of computer systems 1100. This disclosure contemplates computer system 1100 taking any suitable physical form. As example and not by way of limitation, computer system 1100 may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, a personal digital assistant (PDA), a server, a tablet computer system, or a combination of two or more of these. Where appropriate, computer system 1100 may include one or more computer systems 1100; be unitary or distributed; span multiple locations; span multiple machines; span multiple data centers; or reside in a cloud, which may include one or more cloud components in one or more networks. Where appropriate, one or more computer systems 1100 may perform without substantial spatial or temporal limitation one or more steps of one or more methods described or illustrated herein. As an example and not by way of limitation, one or more computer systems 1100 may perform in real time or in batch mode one or more steps of one or more methods described or illustrated herein. One or more computer systems 1100 may perform at different times or at different locations one or more steps of one or more methods described or illustrated herein, where appropriate.

In particular embodiments, computer system 1100 includes a processor 1102, memory 1104, storage 1106, an input/output (I/O) interface 1108, a communication interface 1110, and a bus 1112. Although this disclosure describes and illustrates a particular computer system having a particular number of particular components in a particular arrangement, this disclosure contemplates any suitable computer system having any suitable number of any suitable components in any suitable arrangement.

In particular embodiments, processor 1102 includes hardware for executing instructions, such as those making up a computer program. As an example and not by way of limitation, to execute instructions, processor 1102 may retrieve (or fetch) the instructions from an internal register, an internal cache, memory 1104, or storage 1106; decode and execute them; and then write one or more results to an internal register, an internal cache, memory 1104, or storage 1106. In particular embodiments, processor 1102 may include one or more internal caches for data, instructions, or addresses. This disclosure contemplates processor 1102 including any suitable number of any suitable internal caches, where appropriate. As an example and not by way of limitation, processor 1102 may include one or more instruction caches, one or more data caches, and one or more translation lookaside buffers (TLBs). Instructions in the instruction caches may be copies of instructions in memory 1104 or storage 1106, and the instruction caches may speed up retrieval of those instructions by processor 1102. Data in the data caches may be copies of data in memory 1104 or storage 1106 for instructions executing at processor 1102 to operate on; the results of previous instructions executed at processor 1102 for access by subsequent instructions executing at processor 1102 or for writing to memory 1104 or storage 1106; or other suitable data. The data caches may speed up read or write operations by processor 1102. The TLBs may speed up virtual-address translation for processor 1102. In particular embodiments, processor 1102 may include one or more internal registers for data, instructions, or addresses. This disclosure contemplates processor 1102 including any suitable number of any suitable internal registers, where appropriate. Where appropriate, processor 1102 may include one or more arithmetic logic units (ALUs); be a multi-core processor; or include one or more processors 1102. Although this disclosure describes and illustrates a particular processor, this disclosure contemplates any suitable processor.

In particular embodiments, memory 1104 includes main memory for storing instructions for processor 1102 to execute or data for processor 1102 to operate on. As an example and not by way of limitation, computer system 1100 may load instructions from storage 1106 or another source (such as, for example, another computer system 1100) to memory 1104. Processor 1102 may then load the instructions from memory 1104 to an internal register or internal cache. To execute the instructions, processor 1102 may retrieve the instructions from the internal register or internal cache and decode them. During or after execution of the instructions, processor 1102 may write one or more results (which may be intermediate or final results) to the internal register or internal cache. Processor 1102 may then write one or more of those results to memory 1104. In particular embodiments, processor 1102 executes only instructions in one or more internal registers or internal caches or in memory 1104 (as opposed to storage 1106 or elsewhere) and operates only on data in one or more internal registers or internal caches or in memory 1104 (as opposed to storage 1106 or elsewhere). One or more memory buses (which may each include an address bus and a data bus) may couple processor 1102 to memory 1104. Bus 1112 may include one or more memory buses, as described below. In particular embodiments, one or more memory management units (MMUs) reside between processor 1102 and memory 1104 and facilitate accesses to memory 1104 requested by processor 1102. In particular embodiments, memory 1104 includes random access memory (RAM). This RAM may be volatile memory, where appropriate Where appropriate, this RAM may be dynamic RAM (DRAM) or static RAM (SRAM). Moreover, where appropriate, this RAM may be single-ported or multi-ported RAM. This disclosure contemplates any suitable RAM. Memory 1104 may include one or more memories 1104, where appropriate. Although this disclosure describes and illustrates particular memory, this disclosure contemplates any suitable memory.

In particular embodiments, storage 1106 includes mass storage for data or instructions. As an example and not by way of limitation, storage 1106 may include a hard disk drive (HDD), a floppy disk drive, flash memory, an optical disc, a magneto-optical disc, magnetic tape, or a Universal Serial Bus (USB) drive or a combination of two or more of these. Storage 1106 may include removable or non-removable (or fixed) media, where appropriate. Storage 1106 may be internal or external to computer system 1100, where appropriate. In particular embodiments, storage 1106 is non-volatile, solid-state memory. In particular embodiments, storage 1106 includes read-only memory (ROM). Where appropriate, this ROM may be mask-programmed ROM, programmable ROM (PROM), erasable PROM (EPROM), electrically erasable PROM (EEPROM), electrically alterable ROM (EAROM), or flash memory or a combination of two or more of these. This disclosure contemplates mass storage 1106 taking any suitable physical form. Storage 1106 may include one or more storage control units facilitating communication between processor 1102 and storage 1106, where appropriate. Where appropriate, storage 1106 may include one or more storages 1106. Although this disclosure describes and illustrates particular storage, this disclosure contemplates any suitable storage.

In particular embodiments, I/O interface 1108 includes hardware, software, or both, providing one or more interfaces for communication between computer system 1100 and one or more I/O devices. Computer system 1100 may include one or more of these I/O devices, where appropriate. One or more of these I/O devices may enable communication between a person and computer system 1100. As an example and not by way of limitation, an I/O device may include a keyboard, keypad, microphone, monitor, mouse, printer, scanner, speaker, still camera, stylus, tablet, touch screen, trackball, video camera, another suitable I/O device or a combination of two or more of these. An I/O device may include one or more sensors. This disclosure contemplates any suitable I/O devices and any suitable I/O interfaces 1108 for them. Where appropriate, I/O interface 1108 may include one or more device or software drivers enabling processor 1102 to drive one or more of these I/O devices. I/O interface 1108 may include one or more I/O interfaces 1108, where appropriate. Although this disclosure describes and illustrates a particular I/O interface, this disclosure contemplates any suitable I/O interface.

In particular embodiments, communication interface 1110 includes hardware, software, or both providing one or more interfaces for communication (such as, for example, packet-based communication) between computer system 1100 and one or more other computer systems 1100 or one or more networks. As an example and not by way of limitation, communication interface 1110 may include a network interface controller (NIC) or network adapter for communicating with an Ethernet or other wire-based network or a wireless NIC (WNIC) or wireless adapter for communicating with a wireless network, such as a WI-FI network. This disclosure contemplates any suitable network and any suitable communication interface 1110 for it. As an example and not by way of limitation, computer system 1100 may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, computer system 1100 may communicate with a wireless PAN (WPAN) (such as, for example, a BLUETOOTH WPAN), a WI-FI network, a WI-MAX network, a cellular telephone network (such as, for example, a Global System for Mobile Communications (GSM) network), or other suitable wireless network or a combination of two or more of these. Computer system 1100 may include any suitable communication interface 1110 for any of these networks, where appropriate. Communication interface 1110 may include one or more communication interfaces 1110, where appropriate. Although this disclosure describes and illustrates a particular communication interface, this disclosure contemplates any suitable communication interface.

In particular embodiments, bus 1112 includes hardware, software, or both coupling components of computer system 1100 to each other. As an example and not by way of limitation, bus 1112 may include an Accelerated Graphics Port (AGP) or other graphics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination of two or more of these. Bus 1112 may include one or more buses 1112, where appropriate. Although this disclosure describes and illustrates a particular bus, this disclosure contemplates any suitable bus or interconnect.

Herein, a computer-readable non-transitory storage medium or media may include one or more semiconductor-based or other integrated circuits (ICs) (such, as for example, field-programmable gate arrays (FPGAs) or application-specific ICs (ASICs)), hard disk drives (HDDs), hybrid hard drives (HHDs), optical discs, optical disc drives (ODDs), magneto-optical discs, magneto-optical drives, floppy diskettes, floppy disk drives (FDDs), magnetic tapes, solid-state drives (SSDs), RAM-drives, SECURE DIGITAL cards or drives, any other suitable computer-readable non-transitory storage media, or any suitable combination of two or more of these, where appropriate. A computer-readable non-transitory storage medium may be volatile, non-volatile, or a combination of volatile and non-volatile, where appropriate.

Herein, "or" is inclusive and not exclusive, unless expressly indicated otherwise or indicated otherwise by context. Therefore, herein, "A or B" means "A, B, or both," unless expressly indicated otherwise or indicated otherwise by context. Moreover, "and" is both joint and several, unless expressly indicated otherwise or indicated otherwise by context. Therefore, herein, "A and B" means "A and B, jointly or severally," unless expressly indicated otherwise or indicated otherwise by context.

The scope of this disclosure encompasses all changes, substitutions, variations, alterations, and modifications to the example embodiments described or illustrated herein that a person having ordinary skill in the art would comprehend. The scope of this disclosure is not limited to the example embodiments described or illustrated herein. Moreover, although this disclosure describes and illustrates respective embodiments herein as including particular components, elements, feature, functions, operations, or steps, any of these embodiments may include any combination or permutation of any of the components, elements, features, functions, operations, or steps described or illustrated anywhere herein that a person having ordinary skill in the art would comprehend.

What is claimed is:

1. A method comprising:

recording, by a camera of a client device, a video of a region of a first user's skin;

estimating, from the recorded video, a current ratio of ratios (RoR) for the first user corresponding to the first user's current blood-oxygen saturation;

converting the first user's determined RoR to a transformed RoR for the first user based at least in part on a baseline user's RoR determined while generating a trained SpO2 prediction model, wherein the trained SpO2 prediction model is trained to estimate the baseline user's SpO2 value based on an input RoR value from the baseline user; and determining, by the trained SpO2 prediction model and based on the transformed RoR for the first user, the first user's current estimated blood-oxygen saturation.

2. The method of claim 1, wherein the baseline user is selected from a plurality of users prior to training the SpO2 prediction model.

3. The method of claim 1, wherein converting the first user's determined RoR to a transformed RoR for the first user based at least in part on a baseline user's RoR comprises:

determining one or more demographics of the first user;

representing the one or more demographics as a vector;

providing the vector to a deviation model trained to predict a difference in RoR between a candidate user and the baseline user based on an input demographic vector for the candidate user;

determining, by the trained deviation model, a difference in RoR between the first user and the baseline user; and determining the transformed RoR based on a combination of the first user's determined RoR and the determined difference in RoR between the first user and the baseline user.

4. The method of claim 3, wherein the trained deviation model comprises a deviation model trained by:

for each of a plurality of k users:

selecting a ground-truth SpO2 value in a training dataset for that user nearest to a predetermined SpO2 value;

determining a ground-truth RoR value in the training dataset that corresponds to the selected ground-truth SpO2 value;

determining an RoR difference between (1) the ground-truth RoR value for the respective user and (2) a ground-truth RoR value for the baseline user corresponding to a nearest baseline ground-truth SpO2 value to the predetermined SpO2 value;

determining a corresponding vector of demographic information of the respective user; and training the deviation model to output a predicted RoR difference, using the k vectors of demographic information and the k RoR differences.

5. The method of claim 1, wherein converting the first user's determined RoR to a transformed RoR for the first user based at least in part on a baseline user's RoR comprises:

providing the first user's determined RoR to an RoR transformation model specific to the first user and the baseline user, wherein the transformation model is configured to convert the first user's determined RoR to an RoR of the baseline user; and determining, by the transformation model, the transformed RoR.

6. The method of claim 5, wherein the transformation model is created at least in part by:

measuring a ground-truth blood-oxygen saturation value for the first user;

determining a corresponding RoR for the first user, based on a video sample of the first user coincident with the measured ground truth blood-oxygen saturation value;

determining, from a plurality of blood-oxygen saturation values of the baseline user, a particular blood-oxygen saturation value nearest to the measured ground truth blood-oxygen saturation value of the first user;

determining, a baseline RoR of the baseline user corresponding to the particular blood-oxygen saturation value; and defining the transformation model to convert the corresponding RoR for the first user to the baseline RoR of the baseline user.

7. The method of claim 5, wherein the transformation model is created at least in part by:

determining a calibration RoR for the first user, based on a calibration video sample of the first user;

assigning, to the first user and based on one or more of (1) an altitude of the first user and (2) one or more of the first user's demographics, a predetermined blood-oxygen saturation value corresponding to the calibration RoR;

determining, from a plurality of blood-oxygen saturation values of the baseline user, a particular blood-oxygen saturation value nearest to the predetermined assigned blood-oxygen saturation value of the first user;

determining a baseline RoR of the baseline user corresponding to the particular blood-oxygen saturation value; and defining the transformation model to convert the calibration RoR for the first user to the baseline RoR of the baseline user.

8. The method of claim 1, further comprising:

classifying a skin type of the first user; and in response to a determination that the skin type of the first user is greater than a threshold classification, then adjusting one or more camera settings of the camera.

9. The method of claim 8, wherein adjusting the one or more camera settings of the camera comprises increasing one or more of (1) the camera gain and (2) the camera exposure time.

10. The method of claim 1, further comprising:

classifying a skin type of the first user; and in response to a determination that the skin type of the first user is greater than a threshold classification, then increasing an intensity of one or more light sources in the vicinity of the first user.

11. The method of claim 1, further comprising:

detecting, from at least a portion of the video of a region of a first user's skin, one or more current lighting conditions in the vicinity of the first user; and determining whether the current lighting conditions comprise a deviation from a predetermined, ideal lighting condition for estimating SpO2 values; and in response to a determination that the current lighting conditions comprise a deviation from the predetermined, ideal lighting conditions, then adjusting the estimated RoR for the first user.

12. The method of claim 11, wherein the lighting conditions comprise a color-temperature classification, and the predetermined, ideal lighting condition comprises a warm color temperature.

13. The method of claim 11, wherein adjusting the estimated RoR for the first user comprises adjusting, by a trained diffusion model, the estimated RoR to a corrected RoR representing the estimated RoR signal in the ideal lighting condition.

14. The method of claim 1, further comprising:

determining one or more color characteristics of the camera;

transforming the video of the region of the first user's skin to a transformed video, the transformed video representing one or more color characteristics of a baseline camera used to train the trained SpO2 model; and estimating the first user's RoR based on the transformed video.

15. The method of claim 14, wherein transforming the video of the region of the first user's skin to a transformed video comprises:

converting the video of the region of the first user's skin from an RGB color space to a decorrelated color space;

identifying one or more of a light intensity and a color temperature of each frame of the recorded video;

transforming, based on (1) the recorded video, (2) the light intensity, and (3) the color temperature, each frame of the recorded video to a transformed decorrelated color-space frame; and converting each transformed decorrelated color-space frame to a transformed frame in the RGB color space.

16. The method of claim 15, wherein a trained autoencoder model transforms each frame of the recorded video to a transformed decorrelated color-space frame, and wherein the trained autoencoder model is trained on an array of training images comprising (1) a baseline set of images of a scene taken by the baseline camera, each image taken under a corresponding lighting intensity and color temperature and (2) a first set of images of the scene taken by a testing camera, each image in the first set taken coincident with an image in the baseline set, wherein the testing camera and the camera of claim 1 comprise the same model of camera.

17. One or more non-transitory computer readable storage media storing instructions and coupled to one or more processors that are operable to execute the instructions to:

access a recording, made by a camera of a client device, comprising a video of a region of a first user's skin;

estimate, from the recorded video, a current ratio of ratios (RoR) for the first user corresponding to the first user's current blood-oxygen saturation;

convert the first user's determined RoR to a transformed RoR for the first user based at least in part on a baseline user's RoR determined while generating a trained SpO2 prediction model, wherein the trained SpO2 prediction model is trained to estimate the baseline user's SpO2 value based on an input RoR value from the baseline user; and determine, by the trained SpO2 prediction model and based on the transformed RoR for the first user, the first user's current estimated blood-oxygen saturation.

18. The media of claim 17, wherein converting the first user's determined RoR to a transformed RoR for the first user based at least in part on a baseline user's RoR comprises:

determining one or more demographics of the first user;

representing the one or more demographics as a vector;

providing the vector to a deviation model trained to predict a difference in RoR between a candidate user and the baseline user based on an input demographic vector for the candidate user;

determining, by the trained deviation model, a difference in RoR between the first user and the baseline user; and determining the transformed RoR based on a combination of the first user's determined RoR and the determined difference in RoR between the first user and the baseline user.

19. The media of claim 17, wherein converting the first user's determined RoR to a transformed RoR for the first user based at least in part on a baseline user's RoR comprises:

providing the first user's determined RoR to an RoR transformation model specific to the first user and the baseline user, wherein the transformation model is configured to convert the first user's determined RoR to an RoR of the baseline user; and determining, by the transformation model, the transformed RoR.

20. A system comprising:

one or more non-transitory computer readable storage media storing instructions; and one or more processors coupled to the non-transitory computer readable storage media, the one or more processors operable to execute the instructions to:

access a recording, made by a camera of a client device, a video of a region of a first user's skin;

estimate, from the recorded video, a current ratio of ratios (RoR) for the first user corresponding to the first user's current blood-oxygen saturation;

convert the first user's determined RoR to a transformed RoR for the first user based at least in part on a baseline user's RoR determined while generating a trained SpO2 prediction model, wherein the trained SpO2 prediction model is trained to estimate the baseline user's SpO2 value based on an input RoR value from the baseline user; and determine, by the trained SpO2 prediction model and based on the transformed RoR for the first user, the first user's current estimated blood-oxygen saturation.

* * * * *